United States Patent [19]
West

[11] Patent Number: 5,319,421
[45] Date of Patent: Jun. 7, 1994

[54] TONER CONCENTRATION SENSING WITH SELF CALIBRATION

[75] Inventor: Daniel A. West, Boulder Creek, Calif.

[73] Assignee: Xerox Corporation, Stamford, Conn.

[21] Appl. No.: 949,188

[22] Filed: Sep. 22, 1992

[51] Int. Cl.$^5$ .......................................... G03G 15/10
[52] U.S. Cl. ..................... 355/256; 118/660; 118/689; 346/140 R; 355/208; 355/246; 355/326 R
[58] Field of Search ............... 355/256, 246, 245, 208, 355/326 R, 327; 346/157, 140 R; 364/509; 118/645, 659–660, 688, 689, 690, 691; 356/433, 435–442; 222/DIG. 1; 354/298, 324

[56] References Cited

U.S. PATENT DOCUMENTS

| | | | |
|---|---|---|---|
| 3,354,802 | 11/1967 | Doucette et al. | |
| 3,677,222 | 7/1972 | Komori et al. | 118/691 |
| 3,698,356 | 10/1972 | DuBois et al. | 118/691 |
| 3,712,203 | 1/1973 | Kishi et al. | 355/246 |
| 3,807,872 | 4/1974 | Pronier | 356/410 |
| 4,119,989 | 10/1978 | Carvalko et al. | 354/298 |
| 4,166,702 | 9/1979 | Okamoto et al. | 356/440 |
| 4,222,497 | 9/1980 | Lloyd et al. | 222/57 |
| 4,310,238 | 1/1982 | Mochizuki et al. | 355/256 X |
| 4,660,152 | 4/1987 | Downing et al. | 364/509 |
| 4,796,051 | 1/1989 | Monkelbaan et al. | 355/327 |
| 4,799,452 | 1/1989 | Day | 118/645 |
| 4,981,362 | 1/1991 | deJong et al. | 356/436 |
| 4,987,429 | 1/1991 | Finley et al. | 346/157 |

FOREIGN PATENT DOCUMENTS 62-78580 4/1987 Japan.

Primary Examiner—A. T. Grimley
Assistant Examiner—Shuk Y. Lee
Attorney, Agent, or Firm—Lisa M. Yamonaco

[57] ABSTRACT

A self calibrating system for measuring concentration of a material carried in a fluid medium. The system has a flow cell means for measuring the transmissivity of a fluid medium passing therethrough, a first means for delivering a first fluid containing material carried in fluid medium, and a second means for delivering a clear dispersant fluid. The system also has a switching means for selecting among the delivering means, the switching means connecting one of the delivering means to the flow cell means, a first memory means for storing a table of C1 concentration and associated voltage values corresponding to the transmissivity measurement of the first fluid, a second memory means for storing a table of C2 concentration and associated voltage values corresponding to the transmissivity measurement of the clear dispersant, and calculating means for adding a C1 concentration value from the C1 table to a C2 concentration value from the C2 table thereby determining the concentration of the material in the fluid medium being measured by the flow cell. The system can have additional delivering means as is required for color printing. Also provided is a method for measuring the concentration of toner particles carried in a fluid medium during a calibration period and during run-time use.

7 Claims, 6 Drawing Sheets

| $V_c(W1)_1$ | $V_c(W1)_2$ | $V_c(W1)_3$ | $V_c(W1)_4$ | $V_c(W1)_5$ | $V_c(W1)_6$ | $V_c(W1)_7$ | $V_c(W1)_8$ | $V_c(W1)_9$ | $V_c(W1)_{10}$ | ← 81 |
| $V_c(W2)_1$ | $V_c(W2)_2$ | $V_c(W2)_3$ | $V_c(W2)_4$ | $V_c(W2)_5$ | $V_c(W2)_6$ | $V_c(W2)_7$ | $V_c(W2)_8$ | $V_c(W2)_9$ | $V_c(W2)_{10}$ | ← 82 |
| $C2(A)_1$ | $C2(A)_2$ | $C2(A)_3$ | $C2(A)_4$ | $C2(A)_5$ | $C2(A)_6$ | $C2(A)_7$ | $C2(A)_8$ | $C2(A)_9$ | $C2(A)_{10}$ | ← 83 |
| $C2(B)_1$ | $C2(B)_2$ | $C2(B)_3$ | $C2(B)_4$ | $C2(B)_5$ | $C2(B)_6$ | $C2(B)_7$ | $C2(B)_8$ | $C2(B)_9$ | $C2(B)_{10}$ | ← 84 |
| $C2(C)_1$ | $C2(C)_2$ | $C2(C)_3$ | $C2(C)_4$ | $C2(C)_5$ | $C2(C)_6$ | $C2(C)_7$ | $C2(C)_8$ | $C2(C)_9$ | $C2(C)_{10}$ | ← 85 |
| $C2(D)_1$ | $C2(D)_2$ | $C2(D)_3$ | $C2(D)_4$ | $C2(D)_5$ | $C2(D)_6$ | $C2(D)_7$ | $C2(D)_8$ | $C2(D)_9$ | $C2(D)_{10}$ | ← 86 |

FIG. 5

| 91 | 92 | 93 | 94 | 95 | 96 | 97 | 98 |
|---|---|---|---|---|---|---|---|
| $V(A)_{10}$ | $C1(A)_{10}$ | $V(B)_{10}$ | $C1(B)_{10}$ | $V(C)_{10}$ | $C1(C)_{10}$ | $V(D)_{10}$ | $C1(D)_{10}$ |
| $V(A)_9$ | $C1(A)_9$ | $V(B)_9$ | $C1(B)_9$ | $V(C)_9$ | $C1(C)_9$ | $V(D)_9$ | $C1(D)_9$ |
| $V(A)_8$ | $C1(A)_8$ | $V(B)_8$ | $C1(B)_8$ | $V(C)_8$ | $C1(C)_8$ | $V(D)_8$ | $C1(D)_8$ |
| $V(A)_7$ | $C1(A)_7$ | $V(B)_7$ | $C1(B)_7$ | $V(C)_7$ | $C1(C)_7$ | $V(D)_7$ | $C1(D)_7$ |
| $V(A)_6$ | $C1(A)_6$ | $V(B)_6$ | $C1(B)_6$ | $V(C)_6$ | $C1(C)_6$ | $V(D)_6$ | $C1(D)_6$ |
| $V(A)_5$ | $C1(A)_5$ | $V(B)_5$ | $C1(B)_5$ | $V(C)_5$ | $C1(C)_5$ | $V(D)_5$ | $C1(D)_5$ |
| $V(A)_4$ | $C1(A)_4$ | $V(B)_4$ | $C1(B)_4$ | $V(C)_4$ | $C1(C)_4$ | $V(D)_4$ | $C1(D)_4$ |
| $V(A)_3$ | $C1(A)_3$ | $V(B)_3$ | $C1(B)_3$ | $V(C)_3$ | $C1(C)_3$ | $V(D)_3$ | $C1(D)_3$ |
| $V(A)_2$ | $C1(A)_2$ | $V(B)_2$ | $C1(B)_2$ | $V(C)_2$ | $C1(C)_2$ | $V(D)_2$ | $C1(D)_2$ |
| $V(A)_1$ | $C1(A)_1$ | $V(B)_1$ | $C1(B)_1$ | $V(C)_1$ | $C1(C)_1$ | $V(D)_1$ | $C1(D)_1$ |

FIG. 6

TONER CONCENTRATION SENSING WITH SELF CALIBRATION

BACKGROUND OF THE INVENTION

This invention relates to a system and method for automatically sensing, monitoring and adjusting the concentration of a material carried in a body of fluid. More particularly, the invention relates to a system and method for automatically sensing, monitoring and adjusting the toner concentration within liquid solution in an electrographic printing environment utilizing self calibration.

The electrographic recording process, for which the method of this invention is particularly applicable, includes the steps of forming an electrostatic latent image upon a recording medium and subsequently making the latent image visible. The recording medium, usually provided in web form, has a dielectric and a conductive surface and may be a coated paper, a polyester based transparent film, or other suitable material on which an electrostatic latent image is formed by means of a plurality of writing electrodes or styli physically positioned on one side thereof to electrically address the dielectric surface as the medium travels therepast through a recording station. Opposite the dielectric surface of the recording medium there is a conductive surface which in some cases is grounded. When the potential difference between the conductive surface and the recording elements is raised above a threshold level, on the order of several hundred volts, an electrostatic charge is deposited on the dielectric surface of the recording medium as the medium passes by the recording elements.

Subsequently the latent image is made visible during the development step by applying liquid or dry toner to the recording medium. The recording medium is contacted by a thin film of developer material out of which the toner particles are electrostatically attracted to the regions of electrostatic charge on the medium. These toner particles often are suspended in a liquid solution at a preferred concentration. As many images are developed, the particles suspended in the liquid become depleted causing the concentration of the particles in the liquid to be reduced. Therefore, as will become apparent, it is important to monitor the depletion of these particles as the concentration of the liquid changes and to compensate for such depletions as they occur.

Electrostatic plotters are available in a monochrome mode, including a single recording station and a single development station dispensing a single color toner, usually black. Also, electrostatic color plotters are available to produce full color plots by the sequential overlaying of a series of separate color images (yellow, cyan, magenta and black) to produce a full spectrum of colors.

There have been three basic approaches to color separation imaging. In the first, a series of images are formed sequentially each by means of a dedicated recording head and development station. In the second, a single recording head forms each color separation image on the recording medium which is then advanced past one of several development stations. Then, the recording medium is returned to the recording head for receiving the next color separation image and is advanced to the next development station. This process of advancing and returning the recording medium through the apparatus minimizes the number of recording heads and obviates the need for their critical alignment with respect to one another.

The third approach to color separation imaging is set forth in U.S. Pat. No. 4,799,452 to Day, U.S. Pat. No. 4,987,429 to Finley et al. and U.S. Pat. No. 4,796,051 to Monkelbann et al. Here a single recording head forms each color separation image on the recording medium, as in the second approach described above, however only one toner fountain is used for development whereby all toners pass through the same fountain which is purged between colors.

Each of the electrographic systems described above have to compensate for the changes in the concentration of the toner. In liquid toner electrostatic plotters, toner concentration is often measured optically. The liquid toner is pumped between two closely spaced, parallel, clear windows, forming a thin layer through which light is passed. Toner concentration is proportional to the amount of light registered at an optical sensor. A full description of such a system is described in U.S. Pat. No. 4,222,497 to Lloyd et al. which is assigned to a common assignee and hereby incorporated by reference. Various other systems using this approach are described in U.S. Pat. Nos.: 4,981,362; 4,660,152; 4,166,702; 4,119,989; 3,807,872; 3,712,203; 3,698,356; 3,677,222; and 3,354,802. Typically, color electrographic systems have four such windows, one for each color (e.g. black, cyan, magenta, yellow).

The accuracy of concentration measurement is highly sensitive to the thickness of the toner layer, i.e. the "window thickness", as well as variations in the optical properties of the toner being measured. This requires very tight tolerances on the window (e.g. 20±1 mil) which, realistically, can only be met by sorting parts. Calibration of a plotter would be performed on the assembly line to compensate for the initial properties of the elements being used in that plotter. This type of calibration process does not take into account element properties that change or degrade over time. In addition, any improvements in toner formulation which affect optical properties cannot be easily implemented. Therefore, it would be advantageous to have a method by which a plotter can automatically compensate, or "self calibrate" for variations in window thickness, and toner optical properties. This would improve the accuracy of concentration measurement, decrease the cost of manufacturing windows, and allow improvements in toner formulation to be easily implemented. Such a calibration could be performed upon request.

Another problem with optical toner concentration measurement is window staining by the toner over long periods of time. This causes attenuation of the light, which can be misinterpreted as increased toner concentration, leading to measurement error. The same effect is caused by variations and aging in the optics and electronics. Systems of the past have taken a measurement of the window in the absence of toner to get a measurement of the staining of the window. However, a preferred method for automatic compensation for these effects can be accomplished by measuring the light attenuation with 0% concentration toner (i.e. clear ISO-PAR ® from Exxon Corp.) being circulated through the window. Such a system could use one window for measuring all toner values, including the value for the clear solution, and problems of residual toner on the window would be decreased due to the flushing effect of the clear solution.

One skilled in the art knows that the attenuation of the light is a logarithmic function of the toner concentration. One way to determine toner concentration is to measure the light attenuation, then perform a logarithmic calculation. Electrographic plotters are typically stand alone machines which use a microprocessor, or CPU (Central Processing Unit) for control, therefore, the logarithmic calculation required would be done by the microprocessor. The toner concentration measurement needs to take place during plot generation, or run-time mode, because that is when the toner is flowing through the measurement window.

Unfortunately, taking logarithms takes much longer than simple calculations, like addition. The CPU is very busy doing other functions at the same time as the concentration measurement, for instance; moving paper, handling plot data and several other tasks. It is so busy that only a few milliseconds at a time can be devoted to sensing concentration. One possible way to handle the problem is to add a coprocessor chip to do the logarithmic calculation, but the cost of this type of solution is prohibitive.

Therefore it would be advantageous to have a method for implementing toner concentration measurement which requires no logarithmic calculations during the run-time mode. Such a method could implement a table look-up scheme which can easily be done in the few milliseconds the CPU has available. One approach could be to put log table information into the look-up table, but this would require a huge amount of memory. However, a preferred approach would be to have a method which uses a self calibration routine that measures the actual window, optics, electronics and toner in the machine and creates very small look-up tables during a calibration time. This calibration could be performed upon request when the machine is idle and the tens of milliseconds of computational time required for logarithms is available. The calibration routine could generate small tables which can be accessed quickly during the run-time operation.

These small tables could be specific to the calibrated properties for a given plotter, and also contain the information needed to compensate for further window staining and electronics aging. As will be seen, concentration measurement during plot generation could be reduced to looking up values in two tables and adding them together. This look up scheme and corresponding addition would require less memory and fewer computational cycles than a system calculating the logarithmic values on the fly. Furthermore, it will be seen that such tables can be recreated at power-on by storing several key parameters, used during calculation of the values for the look-up tables, thereby saving nonvolatile memory space.

SUMMARY OF THE INVENTION

In accordance with the present invention, provided is a system for measuring concentration of a material carried in a fluid medium, comprising: flow cell means through which the fluid medium passes for measuring the transmissivity of a fluid medium passing through the flow cell means; a first means for delivering a first fluid containing material carried in fluid medium; a second means for delivering a clear dispersant fluid; a switching means for selecting among the delivering means, the switching means connecting one of the delivering means to the flow cell means; a first memory means for storing a table of C1 concentration and associated voltage values corresponding to the transmissivity measurement of the first fluid through the flow cell means; a second memory means for storing a table of C2 concentration and associated voltage values corresponding to the transmissivity measurement of the clear dispersant through the flow cell means; and calculating means for adding a C1 concentration value from the C1 table to a C2 concentration value from the C2 table thereby determining the concentration of the material in the fluid medium being measured by the flow cell. The system is self calibrating and can accommodate a plurality of colors.

Also, provided is method for measuring the concentration of toner particles carried in a fluid medium in an electrographic printing device, the printing device having a plurality of color toners, the printing device having a flow cell where each color toner passes through, the flow cell having at least one windowing area for measuring a voltage of each of the toners passing through the window, the printing device having memory for storing results of a calibration, the results of calibration being stored in a C1 look-up table and a C2 look-up table, the C1 table having color voltage values and corresponding color concentration values for each of the color toners, the C2 table having clear dispersant voltage values and corresponding clear dispersant concentration values, including the steps of: a) measuring the transmissivity of clear dispersant through the flow cell resulting in a clear voltage value; b) reading a clear dispersant concentration value from the C2 table corresponding with the clear voltage value; c) measuring the transmissivity of the color toner through the flow cell resulting in a toner voltage value; d) reading a color toner concentration value from the C1 table corresponding with the toner voltage value; e) adding the clear dispersant concentration value to the color toner concentration value resulting in a total concentration value; f) using the total concentration value to adjust the concentration of the material in the fluid medium corresponding to the color toner; and repeating steps a through f for each of the color toners in the printing device.

BRIEF DESCRIPTION OF THE DRAWINGS

In the drawings:

FIG. 2B is a sectional view taken substantially in the direction of arrows 2—2 of FIG. 2a.

FIG. 5 is an exemplary C2 look-up table; and

FIG. 6 is an exemplary C1 look-up table.

DETAILED DESCRIPTION OF THE INVENTION

In describing this invention, reference will be made to its application to the toner development system used in an electrographic printing or plotting environment. However, it will be apparent to those skilled in the art that the methods of this invention are equally applicable to any system wherein the concentration of material in a fluid carrier, or medium needs to be monitored and periodically adjusted to maintain a predetermined level of material concentrate in the fluid.

Figure 1:
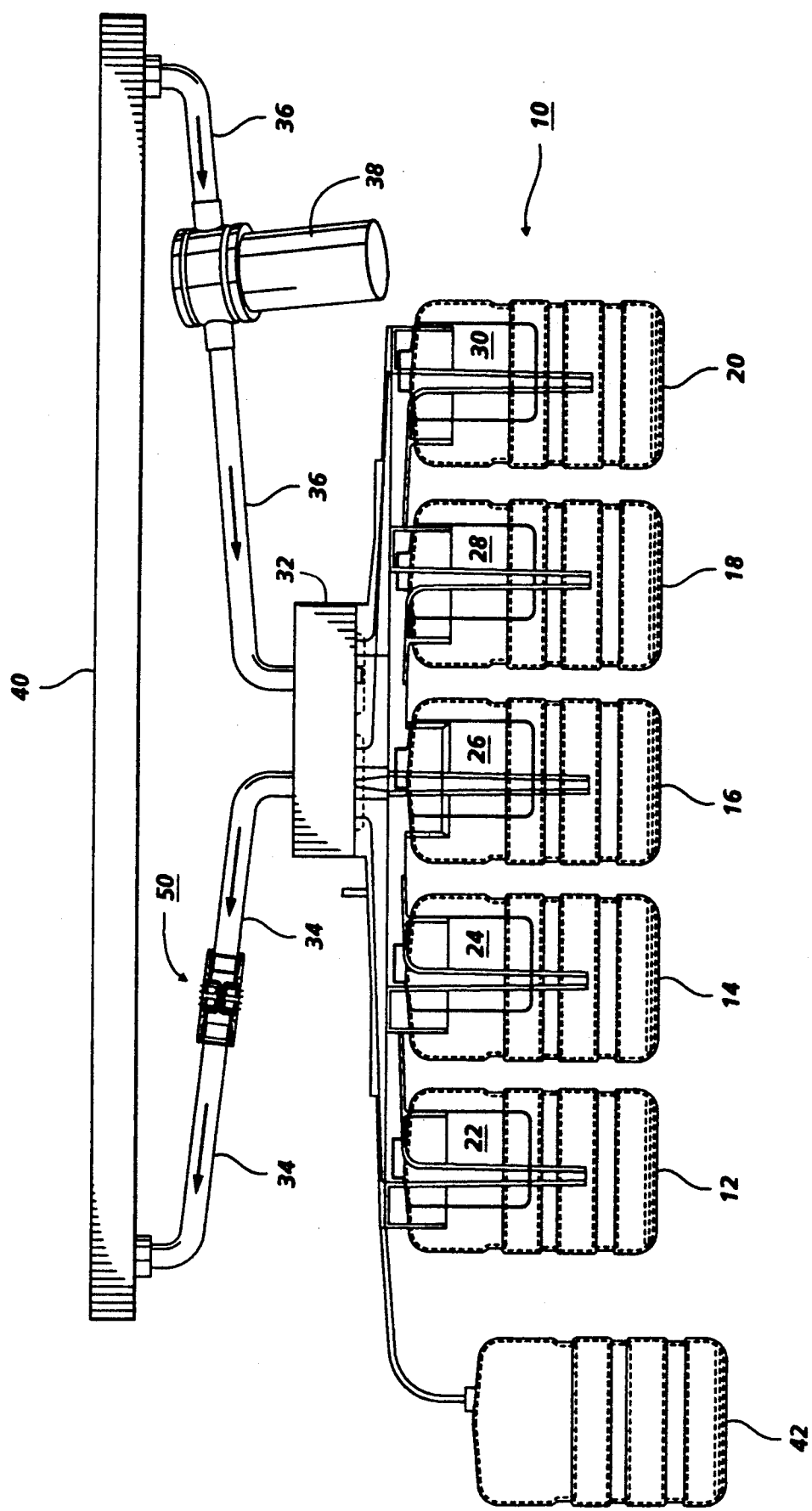
FIG. 1 is a schematic front view of the toning system of an electrographic plotting apparatus utilizing the present invention.

Referring to FIG. 1, shown is a front view of toning system 10 of a color electrostatic plotter which uses liquid toner. As will be seen, each color toner circulates through common plumbing of toning system 10 as shown, and the common plumbing is flushed with a clear dispersant, such as ISOPAR ® (Exxon Corp.) between color passes.

Toning system 10 houses toner solution bottles 12, 14, 18, 20, and clear dispersant bottle 16. During development of an electrostatic image onto a medium, each toning bottle is connected in turn to the common plumbing by valve 32. Due to the action of pump 38, the toner solution, for example from bottle 20, is drawn through valve 32 and tube 34 in the direction indicated by the arrow, and into fountain 40 where the toner solution comes in contact with the print medium. Excess toner solution is then returned to bottle 20 through tube 36 and valve 32. As will be discussed later, the toner solution passing through tube 34 is measured by concentrate window sensor 50. Next, valve 32 connects clear dispersant bottle 16 to the common plumbing, allowing a clear dispersant such as ISOPAR ® to be used. Dispersant from bottle 16 flushes all of the common plumbing of system 10, including valve 32, tubes 34, 36, fountain 40 and concentrate sensor 50, and the dirty dispersant is directed to bottle 42. The process of shifting valve 32, toning and flushing the plumbing is repeated for each color pass of the plot. In another section of the electrographic plotter which is not shown, the dirty fluid in bottle 42 is cleaned and returned to bottle 16.

Each time a plot is made and toner solution is used, the concentration of solids in toner solution bottles 12, 14, 18, 20 becomes depleted. Image quality depends on maintaining the correct concentration of solids in the toner solution. In the present invention, this is all done automatically by measuring toner concentration utilizing concentrate sensor 50, then adding high solids concentrate to the toner solution as required. As seen in FIG. 1, each toner solution bottle 12, 14, 18, 20 has an associated concentrate solution bottle 22, 24, 28, 30 respectively. Concentrate from bottles 22, 24, 28, 30 is added to the toner solutions of bottles 12, 14, 18, 20 to bring the toner solution in these bottles back to a desired concentration. In a similar manner, when the clear dispersant in bottle 16 becomes depleted, new dispersant from bottle 26 is added to the dispersant in bottle 16.

Figure 2A:
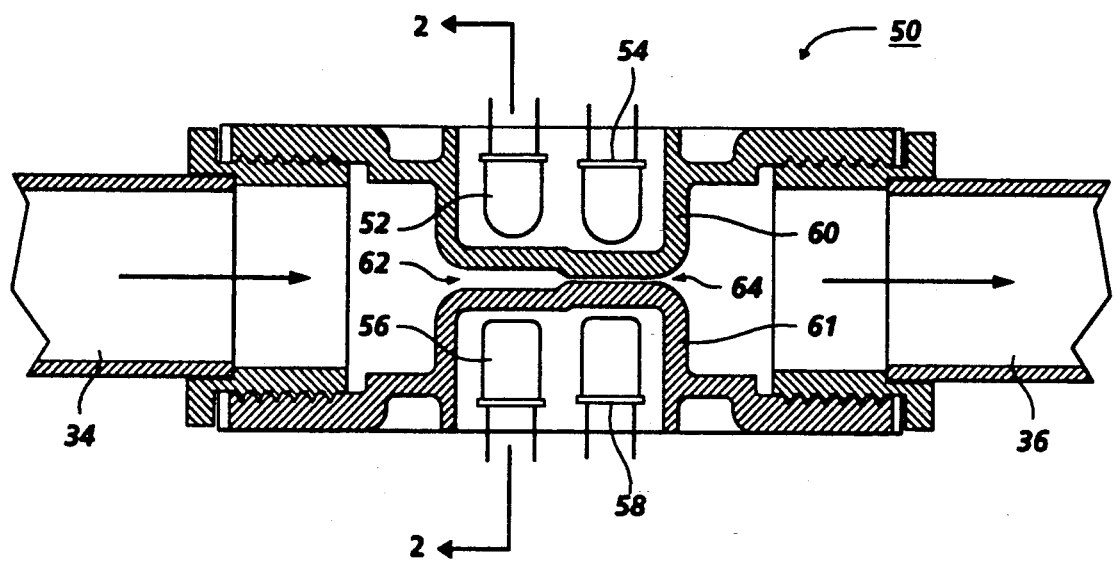
FIG. 2a is a magnified schematic diagram of a concentrate sensor utilized in the present invention.
Figure 2B:
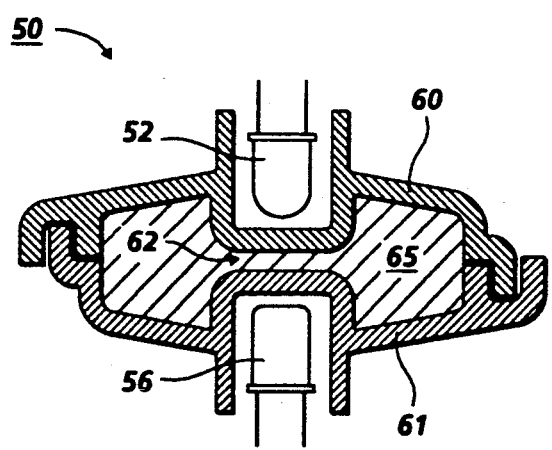

As discussed in the background, toner solution concentration can be measured optically. In this case, and referring to FIGS. 2a and 2b, toner solution is passed through concentrate sensor 50. Concentrate sensor 50 has a large flow area 65 (identified by the crosshatching in FIG. 2b) whereby fluid is free to flow easily. For measurement purposes, concentrate sensor 50 has two windowing areas 62 and 64 formed by window molds 60, 61. Note that the thickness of windowing area 62 (e.g. 55 mils) is larger than that of windowing area 64 (e.g. 15 mils). In this system, two different sized windowing areas are used to compensate for the difference in the optical properties of the different color toner solutions. As will be seen, windowing area 62 will be used to measure the optical properties of the yellow, cyan, and magenta toner solutions whereas windowing area 64 will be used to measure the optical properties of the black toner solution. It can be appreciated that a different sized windowing area can be utilized to correspond with each toner solution being measured in a system. Furthermore, concentrate sensor 50 has LEDs 52, 54 and corresponding photoreceptors 56, 58 for measuring the optical properties of the toner solutions that pass through windowing areas 62, 64.

In order for the optical property measurements to be used during run-time operation to adjust the concentration of the toner solutions, the electrographic plotter has to first be calibrated. As will be seen, the self calibration, window staining compensation and simplified methods described herein will improve the accuracy of concentration measurement and save money. Calibration is activated upon demand of a user. It is important to note that prior to calibration, the concentration of the toner solutions in bottles 12, 14, 18, 20 of FIG. 1 is either known, or at a level satisfactory for the system, because the self calibration routine utilizes these concentrations and adjusts the values thereto. The intention is to keep the toner solutions at a known concentration, thus it is best to start out with those known concentrations before requesting a calibration. It can be understood by those skilled in the art that some limitations apply to the system. These limitation are caused by optical elements used or by range of toner concentration specified.

At the end of the assembly line, and every time the user puts new toner in the machine (roughly twice per year), the calibration routine is used. If only one toner solution bottle is being changed, the user can request calibration for only that particular color, maintaining the calibration values for the other colors in the system. A plotter can be built having no manual adjustments, and the end user does not have to care about possible future changes in toner because the machine adjusts itself. The only user interaction required is to start the internal self calibration routine whenever the toner is changed.

As discussed in the background, all the time consuming math due to the logarithmic operations, is in the calibration routine, which is only used a few times per year. As will be seen, the calibration routine produces approximately thirty parameters that are stored in nonvolatile memory. Look-up tables generated during calibration can be quickly recreated from these parameters on power up. This approach minimizes nonvolatile memory space used.

Figure 3:
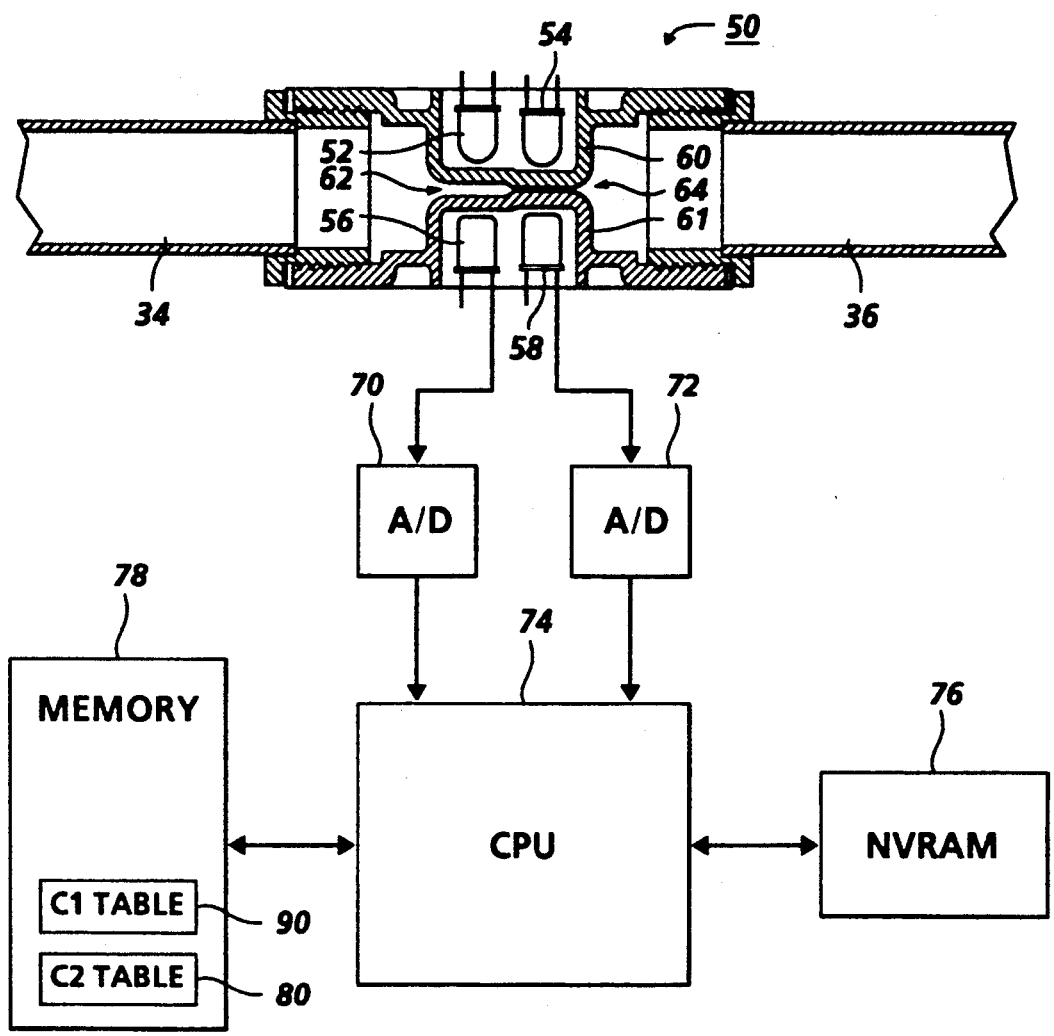
FIG. 3 is a block diagram showing the connection of the concentrate sensor of FIG. 2 with a selection of electronics of an electrographic plotter.

Referring now to FIGS. 3, 4, 5 and 6, the calibration routine will be described in detail. Liquid toner solution is pumped between two parallel, clear windows in concentration sensor 50 formed by window mold sections 60, 61. For the following explanation, let Window 1 (W1) be the window paralleling windowing area 62 and Window 2 (W2) be the window paralleling windowing area 64. Referring especially to FIG. 3, for window 1, the light from LED 52 energizes photoreceptor 56 causing a voltage to be fed into A/D converter 70. For Window 2, the light from LED 54 energizes photoreceptor 58 causing a voltage to be fed into A/D converter 72. The voltages are converted by A/D converters 70, 72 and used by CPU 74 in the calibration process and in the run-time mode.

Light (such as from LEDs 52, 54) passing through the toner, or toner solution, is attenuated according to the equation (Beer-Lambert Law), $$\frac{V}{V_c} = e^{-C c x} \tag{1}$$

where:

V = voltage from photosensor (56 or 58) when toner is passed between the windows ("toner voltage")

Vc = voltage from photosensor with 0% toner (i.e. ISO-PAR ®) is passed between the windows ("clear voltage")

C = toner concentration, by weight (e.g. for 0.7% toner, C=0.007)

$\epsilon$ = optical absorption coefficient of toner x = distance between two parallel windows, i.e. toner thickness.

Any attenuation in light caused by window staining or variations/aging of the optics and electronics will affect both the toner voltage, V, and the clear voltage, Vc, by the same factor. Taking the ratio, V/Vc, automatically compensates for these effects.

Solving equation (1) for C, $$C = -\frac{\ln(V/Vc)}{\epsilon x} \qquad (2)$$

Expanding on equation (2), $$C = -\frac{\ln V}{\epsilon x} + \frac{\ln Vc}{\epsilon x} \qquad (3)$$

Let $$C1 = -\frac{\ln V}{\epsilon x}, \quad C2 = \frac{\ln Vc}{\epsilon x} \qquad (4)$$

Equation (3) becomes, $$C = C1 + C2 \qquad (5)$$

equation 5 is the basis of the concentration sensing method. As will be seen, during the run-time mode, the machine measures V for each color and Vc for the clear voltage, then looks up values for C1 and C2 in tables created during calibration. Tables 80, 90 are stored in memory 78 for later use. Concentration can then be determined without doing any logarithmic calculation.

The look-up tables are of the form:

C1 table (toner voltage table)

$$\begin{array}{cccc} V_1 & V_2 & \ldots & V_n \\ C1_1 & C1_2 & \ldots & C1_n \end{array} \qquad (6)$$

There are n values of V and C1 for each toner color.

C2 table (clear voltage table)

$$\begin{array}{cccc} Vc_1 & Vc_2 & \ldots & Vc_m \\ C2_1 & C2_2 & \ldots & C2_m \end{array} \qquad (7)$$

There are m values of Vc for each window (a system may have different thickness windows for different toner colors), and m values of C2 for each toner color. Note that m and n are numbers that depend on the range of toner concentration to be measured and the desired resolution. Larger values will give a wider range and/or finer measurement resolution.

Referring to FIG. 5, shown is an exemplary C2 table 80 having rows 81, 82, 83, 84, 85, 86. In this case, m=10, although any value of m can be used depending on system requirements. Row 81 contains clear voltage values for Window 1 denoted by Vc(W1)$_i$ where i is from 1 to 10. Row 82 contains clear voltage values for Window 2 denoted by Vc(W2)$_i$. More window rows would be necessary on systems utilizing more than two windows. In a similar manner, rows 83 through 86 contain values of C2 for colors A, B, C, and D respectively. It can be appreciated that the number of C2 rows in table 80 equals the number of colors used in this particular embodiment and other color systems may use a different number of colors thus a different number of C2 rows.

Referring to FIG. 6, shown is an exemplary C1 table 90 having rows 91, 92, 93, 94, 95, 96, 97, 98. In this case, n=10, although any value of n can be used depending on system requirements. (Also, m from table 80 does not have to equal n in table 90.) Row 91 contains the various voltages of color A denoted by V(A)$_i$ where i is from 1 to 10. Row 92 contains C1 values corresponding to the V values of color A denoted by C1(A)$_i$. The remaining rows contain voltage values and their corresponding C1 values for each color used. Again, as noted above, the number of rows in the C1 table depends on the number of colors being used.

As mentioned above, the intention is to maintain some given predetermined concentration of toner. The assumption for all of the self calibration is that the toner concentration of the toners is known or acceptable before the calibration process begins. Once a calibration is requested, the look-up tables are created during a self calibration routine as described below with reference to FIGS. 4–6. The first step is to request calibration as in step 100.

Next, step 102 states:

Put a known concentration of toner into the plotter, where $C_0$=known concentration (e.g. 0.7%) (or assume a known concentration of toner is in the plotter).

Next, step 104 states:

Run a color test plot. Measure Vc for each window. Measure V for each color using the correct window for that color.

In this case, the clear voltage, Vc(W1) nominal is determined by measuring the voltage of the clear dispersant through Window 1 and Vc(W2) nominal is determined by measuring the voltage of the clear dispersant through Window 2. Next, each color A, B, C, and D is run through the concentrate sensor and the nominal voltages are determined for each color using the correct window depending on the optical properties of that color. For example, if color A is black, the voltage V(A) nominal would be measured through Window 2, (i.e. the smaller of the two) while the remaining color voltages V(B), V(C), V(D), would be measured through Window 1 due to their optical properties. Note that between each color, the clear dispersant is used to flush and clean the concentrate sensor.

Next, step 106 states:

Determine low limit for clear voltage, Vc, for each window.

$$Vc_L = K_L Vc \text{ (e.g. } K_L = 0.9\text{)} \qquad (8)$$

K is a constant multiplier used to determine the range of voltages that may be read from a table during run-time mode. The nominal voltage multiplier would be K=1. In the example herein, the voltage range is estimated to be ±10%, therefore the lower limit of K, which is $K_L$ would be −10% of nominal or a multiplier of $K_L$=0.9. The range of voltage to be used in the tables depends on the system requirements and the range of ±10% of nominal is strictly for exemplary purposes. Therefore, the value of $Vc_L(W1)$ and $Vc_L(W2)$ is calculated by multiplying the Vc(W1) and Vc(W2) nominal values (from step 104) by 0.9.

Next, step 108 states:

Determine high limit for clear voltage, Vc, for each window.

$$Vc_H = K_H Vc \text{ (e.g. } K_H = 1.1) \tag{9}$$

$K_H = 1.1$ represents the +10% voltage range endpoint. Therefore, the value of $Vc_H(W1)$ and $Vc_H(W2)$ is calculated by multiplying the Vc(W1) and Vc(W2) nominal values (from step 104) by 1.1.

Once the high and low limits of the clear voltages for each window are available, they can be stored in the exemplary C2 table 80 as endpoints. The low limit voltage for Window 1 is stored in row 81 of table 80 as $Vc(W1)_1$. The high limit voltage for Window 1 is stored in row 81 as $Vc(W1)_{10}$. In a similar manner, $Vc_L$ of Window 2 is stored in row 82 as $Vc(W1)_1$ and $Vc_H$ of Window 2 is stored in row 82 as $Vc(W1)_{10}$.

Next, step 110 states:

Calculate ∈x for each color, using V and Vc from the correct window for that color.

$$\epsilon x = -\frac{\ln(V/Vc)}{C_0} = \frac{\ln(Vc/V)}{C_0} \tag{10}$$

An ∈x value for each color can be calculated from the information already known, namely the color voltage values, the clear voltage value and the concentration of the toner. Since ∈x represents the thickness of the windowing area (x) times the optical absorption coefficient of toner (∈), the calculated values of ∈x are a function of the given plotter that is being calibrated because the values of ∈x are being calculated from measured values of voltage and concentration as opposed to window thickness and absorption coefficients. The value of any given ∈x is specific to the voltages and toner concentrations of a given plotter. It is the ability to define ∈x by using measured voltage values and known toner concentrations that enables the tolerances on the window thickness and toner absorption coefficients to be relaxed, and the system to be more flexible.

Next, step 112 states:

Calculate Vc step size for C2 table.

$$\Delta V_c = \frac{Vc_H - Vc_L}{m - 1} \tag{11}$$

The endpoints of rows 81 and 82 have been entered and the next step is to fill in the remaining values for each row. Step 112 is needed to place m equally spaced voltage values (in the example m=10) between the high and low limits which are already in the table.

Next, step 114 states:

Calculate $Vc_i$ values for C2 table.

$$\begin{aligned} Vc_i &= Vc_L + (i - 1)\Delta V_c \\ &= Vc_L + (i - 2)\Delta V_c + \Delta V_c \\ &= Vc_{i-1} + \Delta V_c \end{aligned} \tag{12}$$

($i = 1$ to $m$; one row for each window)

Remaining values for Window 1 are calculated and placed into row 81 and remaining values for Window 2 are calculated and placed into row 82.

Next, step 116 requires a decision.

Depending on how much computational power is available, and the range of Vc, the C2 values can be calculated using logarithms or a linear approximation. Use of a linear approximation depends on how much, and which part, of the logarithmic curve is being approximated. A determination of the maximum error produced by the linear approximation needs to be made, followed by a decision as to whether this maximum error is acceptable.

To aid in the determination of whether to use linear approximation, a method for finding the maximum error can be achieved as follows:

The logarithmic expression is shown in linear approximation equation 1 (L.A. equation 1) as:

$$C2_i = \frac{\ln Vc_i}{\epsilon x} \tag{L.A. eq. 1}$$

($i = 1$ to $m$; one row for each color)

First, connect the points $(Vc_L, \ln Vc_L)$ and $(Vc_H, \ln Vc_H)$ with a straight line. Any point on the line can be found from, $$A = \ln Vc_L + m\Delta V \tag{L.A. eq. 2}$$

where:

$A$ = approximated value of $\ln(Vc_L + \Delta V)$ $m$ = slope of the straight line $= \frac{(\ln Vc_H - \ln Vc_L)}{Vc_H - Vc_L}$ $\Delta V$ = voltage difference from $Vc_L$ The error between the approximated value, A, and the actual value of $\ln(Vc_L + \Delta V)$ is, $$E = A - \ln(Vc_L + \Delta V) = \ln Vc_L + m\Delta V - \ln(Vc_L + \Delta V) \text{ (L.A. eq. 3)}$$

The value of $\Delta V$ where the error will be a maximum can be found by taking the derivative of E with respect to $\Delta V$ and setting it equal to 0.

$$\frac{dE}{d\Delta V} = m - \frac{1}{Vc_L + \Delta V} = 0 \tag{L.A. eq. 4}$$

Solving for $\Delta V$, $$\Delta V = \frac{1}{m} - Vc_L \tag{L.A. eq. 5}$$

Substituting this into equation (L.A. equation 3) will yield the maximum error in the linear approximation.

$$\begin{aligned} E &= \ln Vc_L + m\left(\frac{1}{m} - Vc_L\right) - \ln\left(Vc_L + \frac{1}{m} - Vc_L\right) \\ &= \ln Vc_L + 1 - mVc_L - \ln\left(\frac{1}{m}\right) \end{aligned} \tag{L.A. eq. 6}$$

Putting in the exemplary values $Vc_L = 9$ and $Vc_H = 11$ (i.e. Vc=10, $K_L = 0.9$ and $K_H = 1.1$) into equation (L.A. eq. 5) and (L.A. eq. 6) yields, $$\Delta V = 0.967 \tag{L.A. eq. 7}$$

$$E = -0.005 \quad \text{(L.A. eq. 8)}$$

$$\ln(Vc_L + \Delta V) = 2.299 \quad \text{(L.A. eq. 9)}$$

$$\% \text{ error} = (100)(0.005/2.299) = 0.2\% \quad \text{(L.A. eq. 10)}$$

This is a very small error (e.g. 0.2%) for the given exemplary range of Vc. Note that the linear approximation may not be as good for other ranges of Vc along the logarithmic curve.

Figure 4:
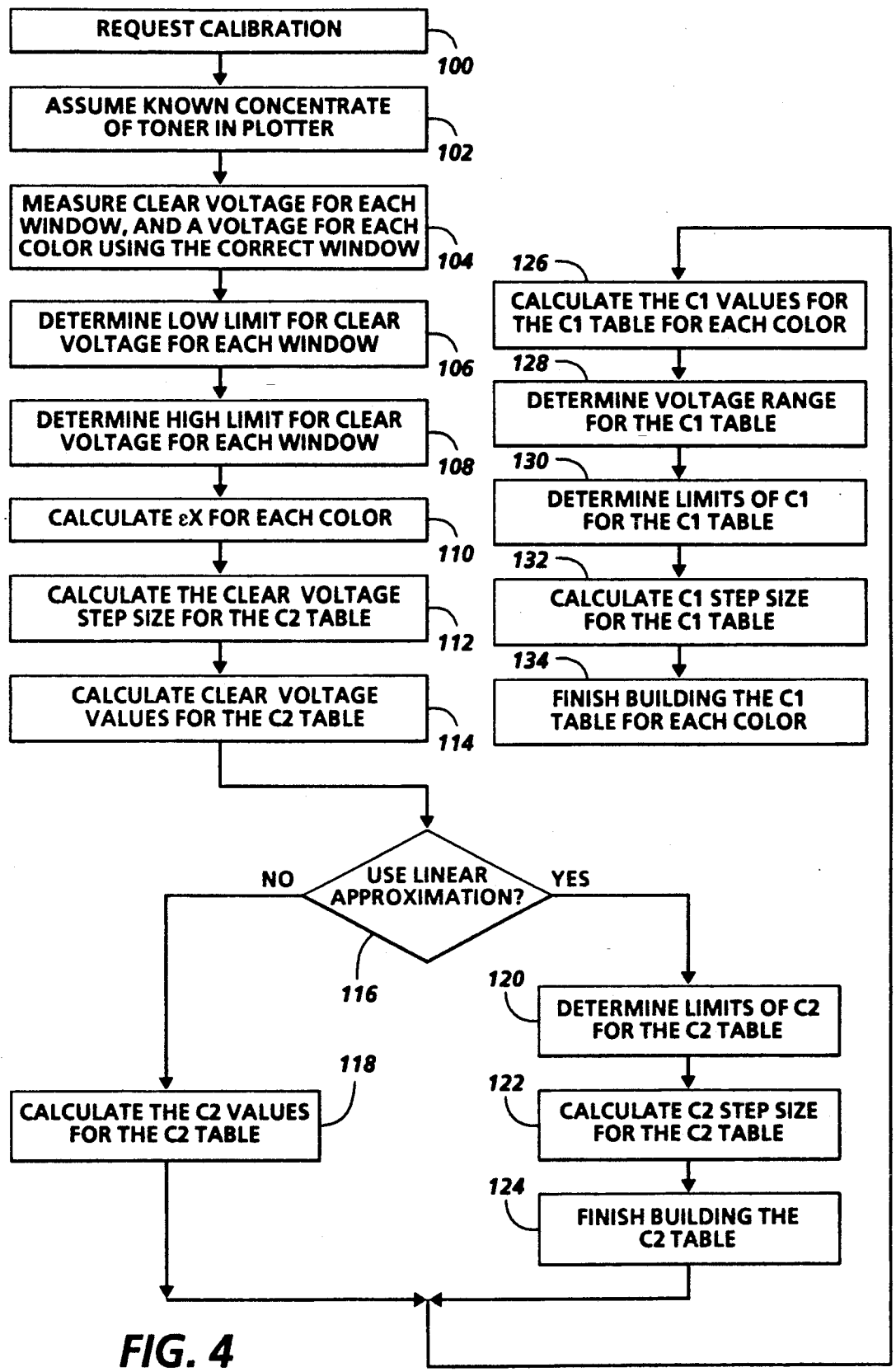
FIG. 4 is a flow chart of the calibration process of the present invention.

Continuing now with FIG. 4, if the answer to step 116 is NO, follow the instructions of step 118.

Step 118 states:
Calculate $C2_i$ values for C2 table.

$$C2_i = \frac{\ln Vc_i}{\epsilon x} \quad (13)$$

($i = 1$ to $m$; one row for each color)

For each color A, B, C, D the C2 values are calculated. Assuming color A is black, the value for clear voltage $Vc_i$ from Window 2 would be used in equation (13) to fill in the corresponding values of $C2(A)_i$. For instance:

$$C2(A)_1 = \frac{\ln V(W2)c_1}{\epsilon x}$$

where $\epsilon x$ was from the value calculated for the black toner in equation (10). If step 118 is used, skip steps 120, 122, and 124 and jump to step 126 described below.

Assuming the linear approximation is used and the answer to step 116 is YES, the following steps will be taken:

Step 120 states:
Determine limits of C2 for C2 table.

$$C2_L = \frac{\ln Vc_L}{\epsilon x} \quad (14)$$

$$C2_H = \frac{\ln Vc_H}{\epsilon x} \quad (15)$$

Calculate $C2(A)_L$ and $C2(A)_H$ using the appropriate $\epsilon x$ for color A and place in row 83 in positions $C2(A)_1$ and $C2(A)_{10}$ respectively. Finish step 120 by calculating the upper and lower limits for the remaining colors (B, C, D) and place the results in rows 84, 85, 86 accordingly.

Step 122 states:
Calculate C2 step size for C2 table.

$$\Delta_{C2} = \frac{C2_H - C2_L}{m - 1} \quad (16)$$

Step size is a function of how many values are required between the endpoints.

Step 124 states:
Finish building C2 table.

$$\begin{aligned} C2_i &= C2_L + (i - 1)\Delta_{C2} \\ &= C2_L + (i - 2)\Delta_{C2} + \Delta_{C2} \\ &= C2_{i-1} + \Delta_{C2} \end{aligned} \quad (17)$$

($i = 1$ to $m$; one row for each color)

In summary, for each color, the first entry for Vc, $Vc_1$, is $Vc_L$, from equation (8). Each subsequent entry, $Vc_i$, is equal to the previous entry, $Vc_{i-1}$, plus a constant, $\Delta_{Vc}$, from equation (11). The first C2 entry, $C2_1$, is $C2_L$, from equation (14). Each subsequent entry, $C2_i$, is equal to the previous entry, $C2_{i-1}$, plus a constant, $\Delta_{C2}$, from equation (16). Therefore, from the calculation of equation (17), $C2_i$ values for colors A, B, C, D are recorded into rows 83, 84, 85, 86 accordingly.

Step 126 states to calculate the C1 values for the C1 table 90, and can be accomplished by using the following steps:

Step 128 states:
Determine voltage range for C1 table. The range of concentration that the table will cover must be specified.

$$C_L = \text{low limit of concentration (e.g. 0.5\%)} \quad (18)$$

$$C_H = \text{high limit of concentration (e.g. 0.9\%)} \quad (19)$$

low limit for voltage (one value for each color) is, $$V_L = Vc_L e^{-C_H \epsilon x} \quad (20)$$

high limit for voltage (one value for each color) is, $$V_H = Vc_H e^{-C_L \epsilon x} \quad (21)$$

First the concentration range for each color toner in the system must be established. For each color, there is some voltage range, from $V_L$ to $V_H$, that the system will have to be able to measure and compensate therefor. The total range of voltages that the C1 table covers must include the range of voltages from different toner concentrations and also the range of clear voltages that can be expected. The calculation for $V_L$ in equation (20) and $V_H$ in equation (21) take into account both factors of clear voltage, $Vc_L$ and $Vc_H$, and concentrations, $C_H$ and $C_L$.

For color A the endpoint voltage, $V_L$, from equation (20) is inserted into row 91 of table 90 as $V(A)_1$ and endpoint voltage, $V_h$, from equation (21) as $V(A)_{10}$, remembering to use the $\epsilon x$ for color A as calculated previously. In a similar manner, the endpoint voltages for colors B, C, and D can be calculated using equations (20) and (21) and placed accordingly in rows 93, 95 and 97 respectively.

Next, step 130 states:
Determine limits of C1 for C1 table.

$$C1_L = -\frac{\ln(V_H)}{\epsilon x} \quad (22)$$

$$C1_H = -\frac{\ln(V_L)}{\epsilon x} \quad (23)$$

Using the endpoint voltage values for each color, endpoint C1 values can be determined using equations (22) and (23). For instance, From the $V_L$ value of the B color $V(B)_1$ of row 93, the endpoint value of $C1(B)_1$ can be determined using equation (22) and placed in row 94 accordingly. Each high and low C1 endpoint values corresponding to the high and low voltage endpoint values for each color are to be calculated and placed in the appropriate rows of table 90.

Next, step 132 states:
Calculate C1 step size for C1 table.

$$\Delta_{C1} = \frac{C1_H - C1_L}{n-1} \quad (24)$$

This step is similar to steps 112, and 122 above whereby equal steps between values in a row are to be determined.

Finally, step 134 states:
Build C1 table.

$$C1_i = C1_L + (i-1)\Delta_{C1} \quad (25)$$
$$= C1_L + (i-2)\Delta_{C1} + \Delta_{C1}$$
$$= C1_{i-1} + \Delta_{C1}$$
($i = 1$ to $n$; one row for each color)

$$V_i = e^{-C1_i \epsilon x} \quad (26)$$
$$= e^{-\{C1_L = (i-1)\Delta_{C1}\}\epsilon x}$$
$$= (e^{-C1_L \epsilon x}) e^{-(i-1)\Delta_{C1} \epsilon x}$$
$$= (e^{-C1_L \epsilon x})(e^{-\Delta_{C1} \epsilon x})^{(i-1)}$$
$$= (e^{-C1_L \epsilon x})(e^{-\Delta_{C1} \epsilon x})^{(i-2)}(e^{-\Delta_{C1} \epsilon x})$$
$$= V_{i-1}(e^{-\Delta_{C1} \epsilon x})$$
($i = 1$ to $n$; one row for each color)

In building the C1 table, for each color, the first C1 entry, $C1_1$, is $C1_L$, from equation (22) and is calculated for each color as in steps 128 and 130. Next, each subsequent entry, $C1_i$, is equal to the previous entry, $C1_{i-1}$, plus a constant, $\Delta_{C1}$, from equation (24) The first entry for V, $V_1$, is $V_H$, from equation (21) and each subsequent entry, $V_i$, is equal to the previous entry, $V_{i-1}$, times a constant, $e^{-\Delta_{C1} \epsilon x}$. At this point, C1 table 90 and C2 table 80 are complete and ready to be used during the run-time mode. As previously mentioned, if fewer than all of the toner bottles are changed, a partial calibration, for only the colors effected, can be run.

In summary, it should be noted that in making the C2 table, start with the limits for clear voltage, split that up into m pieces to come up with the intermediate values for Vc that go into the table, and then calculate C2 values for each $V_C$ value for each color. However, in building the C1 table, start with the limits for voltage, $V_L$ and $V_H$, and then calculate the limit values of C1 associated with those voltages for each color. Next, the intermediate C1 values are calculated in the C1 table and the corresponding V values are calculated from those C1 values. Tables C1 and C2 are filled with values that are specific to the hardware and toner used during calibration. This minimizes the size of the tables, and thus the memory required for table storage because the system does not have to save calibration values for a wide range of possible toner concentrations. Furthermore, the above method requires values for $C_O$, $C_L$, $C_H$, $K_L$, $K_H$, n and m to be determined by the system operator and the rest of the values needed to complete the tables are either measured or calculated.

Referring to FIGS. 3–6, during power-down, the information in memory 78 is lost. However, NVRAM 76 (NonVolatile Random Access Memory) is available for power-down storage of information. It is not necessary to run a calibration each time the plotter is powered down, nor is it necessary to store all of the values in C2 table 80 and C1 table 90 in NVRAM. Once the calibration has been done, tables 80, 90 can be recreated from the values for $V_H$, $e^{-\Delta_{C1} \epsilon x}$, $C1_L$, $\Delta_{C1}$, $Vc_L$, $\Delta_{Vc}$, $C2_L$, $\Delta_{C2}$, n and m for each color where applicable. When the machine is powered down, only these parameters need to be stored in NVRAM 76. Tables 80, 90 can be recreated on power up by performing step 114, step 124, and, step 134, then, restored into memory 78.

Once tables 80, 90 have been created and stored in memory 78, they are available for use during run-time mode. During run-time operation, every time toning system 10 of FIG. 1 is flushed (four times in a color plot, once every several plots for monochrome), the machine reads concentration sensor 50 with clear dispersant running therethrough. It then uses this measurement to adjust itself for window staining, changes in the electronics, etc., at a rate of several times per day. The actual concentration measurement requires two voltage readings, extraction of two values from look-up tables, and one addition. This can easily be done during plot generation expediting system operation.

Referring to FIGS. 1, 3, 5, and 6, an example of run-time operation using the C1 and C2 tables will now be illustrated. For the purpose of example, let color A=black, color B=cyan, color C=magenta and color D=yellow. During a plot, the first color plotted is typically black. To run a black pass, valve 32 is shifted to connect with black toner bottle 14. Toner pump 38 turns on causing the black toner to flow through tube 34 and into fountain 40 for creating an image on the media. Sometime during that imaging process, CPU 74 goes out and samples the voltage created on photosensor 58, for Window 2, corresponding to the concentration of the black toner. CPU 74 samples this voltage several times and takes the average value and uses it as the measurement of the black voltage concentration or V(A) nominal. The clear voltage value Vc(W2) needed for calculation purposes, may be stored in memory from a previous plot or, clear dispersant could be run through the system before the black pass in order to get the clear voltage value.

Note that the case may be that the optics of concentration sensor 50 have changed due to temperature. If the ambient temperature in the room changes by more than a few degrees in between consecutive plots, the stored value for clear voltage Vc may not be appropriate to use with the value for the black toner. Therefore, if it has been more than a few minutes since the last plot, it might be better to do the black pass, measure the black voltage, store it, measure the clear voltage after the black pass, then if concentrate needs to be added to the toner, wait until the next plot before adjusting the black. It may be more accurate than relying on the clear voltage from the last plot, unless the last plot happened just moments before the current plot.

Once appropriate values for the black toner voltage V(A) and the clear voltage Vc(W2) have been obtained, values for C1 and C2 can be extracted from tables 90 and 80 respectively. First, take the Vc(W2) value and find the closest match in row 82 of C2 table 80 and extract the corresponding C2 value. For example, if the closest Vc(W2) value in table 80 is Vc(W2)$_6$, go to row 83, which represents the C2 values for black, and extract C2(A)$_6$. This is now the C2 value. Next, Using the V(A) value, go to table 90 row 91, corresponding to black, and find the closest match to the measured V(A) value and extract the corresponding C1 value. For example, if the closest V(A) value is V(A)$_8$ in the black row 91, extract C1(A)$_8$ from row 92 which now becomes the value for C1. Finally, CPU 74 calculates C=C1+C2 which represents the concentration of the toner.

Once the concentration of the toner is determined, it is up to the system whether concentrate from bottle 24 needs to be added to the toner in bottle 14. Now that the system has a concentration value, it compares this value to the desired concentration value. If the concentration in the bottle is higher then the desired concentration, nothing is done. If it is lower, concentrate is added accordingly. Determination of when to add toner and the amount to add is not within the scope of this invention. However, it should be apparent to someone skilled in the art that there are many ways of determining how much concentrate to add and when to add it. It is suggested that a proportional add system be used.

At the end of the black pass, valve 32 is shifted to connect bottle 16 allowing the plumbing of toning system 10 to be flushed using clear dispersant from bottle 16. During that flush, the value of clear voltage Vc is measured through the next window to be used, and stored to be used by the next color. For the next pass, which for example is cyan, valve 32 is shifted to bottle 12 and the cyan pass is ready to begin. Sometime during the cyan pass, the voltage is again measured for the cyan toner concentration, this time using Window 1, or windowing area 62, on concentration sensor 50. Using the clear voltage Vc(B) and a cyan voltage value V(B), take those values and go into the C2 table 80 to extract a C2 value from row 84, the cyan row, corresponding to Vc(B). Next, go to the C1 table and find the closest voltage for the cyan measurement V(B) and extract the associated C1 value from row 94, the cyan row. Finally, concentration of the cyan toner C=C1+C2 and the determination of concentration adjustment for the toner in bottle 12 can be made accordingly.

After, the cyan pass, valve 32 is again shifted to bottle 16 and toning system 10 is again flushed. The process illustrated above for cyan is then repeated with magenta and yellow. Of course, the C2 value for the magenta pass will be extracted from row 85 of table 80 and the C1 value will be extracted from row 96 of table 90. In a similar manner, the C2 value for the yellow pass will be extracted from row 86 of table 80 and the C1 value will be extracted from row 98 of table 90.

In general, sometime while plotting a particular color, the measurement of toner voltage is made. The system goes through the look up process to get values of C1 and C2, adds them together, and based on the result, decides whether to add toner concentrate accordingly. It is suggested that the concentrate is added before the pass is completed so that is gets mixed in.

In summary, the above described invention solves two basic problems in optical toner concentration measurement. First, measurement errors caused by variations in window thickness, variations and aging in optics and electronics, and changes in toner optical properties are eliminated by having each machine measure and calibrate itself. The calibration routine and its derivation are described in detail above. Secondly, taking logarithms, which are required for toner concentration measurement, during plot generation is prohibitively time consuming using a microprocessor. This dilemma is solved by using a look-up table scheme which can be executed quickly. The tables are created while the machine is idle and the time needed to calculate logarithms is available.

While the invention has been described with reference to the structures disclosed, it is not confined to the details set forth, but is intended to cover such modifications or changes as may come within the scope of the following claims:

I claim:

1. A system for measuring concentration of a material carried in a fluid medium, comprising:
    flow cell means through which said fluid medium passes for measuring transmissivity of a fluid medium passing through said flow cell means;
    a first means for delivering a first fluid containing material carried in fluid medium;
    a second means for delivering a clear dispersant fluid;
    a switching means for selecting among said delivering means, said switching means connecting one of said delivering means to said flow cell means;
    a means for generating a first table of C1 concentration and associated voltage values corresponding to the transmissivity measurement of said first fluid through said flow cell means, said table of C1 concentration and associated voltage values being derived during self calibration of said system;
    a means for generating a table of C2 concentration and associated voltage values corresponding to the transmissivity measurement of said clear dispersant through said flow cell mean, said table of C2 concentration and associated voltage values being derived during self calibration of said system;
    a first memory means for storing said table of C1 concentration and associated voltage values;
    a second memory means for storing said table of C2 concentration and associated voltage values; and
    calculating means for adding a C1 concentration value from said C1 table to a C2 concentration value from said C2 table thereby determining said concentration of said material in said fluid medium being measured by said system.

2. A system for measuring concentration of a material carried in a fluid medium as in claim 1 further comprising:
    a third means for delivering a second fluid containing material carried in fluid medium; and
    said first memory means further including a second table of C1 concentration and voltage values corresponding to the transmissivity measurement of said second fluid through said flow cell means.

3. A system for measuring concentration of a material carried in a fluid medium as in claim 2, further comprising:
    a fourth means for delivering a third fluid containing material carried in fluid medium; and
    said first memory means further including a third table of C1 concentration and voltage values corresponding to the transmissivity measurement of said third fluid through said flow cell means.

4. A system for measuring concentration of a material carried in a fluid medium as in claim 3, further comprising:
    a fifth means for delivering a fourth fluid containing material carried in fluid medium; and
    said first memory means further including a fourth table of C1 concentration and voltage values corresponding to the transmissivity measurement of said fourth fluid through said flow cell means.

5. A method for calibrating an electrographic printing device, said printing device having a plurality of color toners, each of said color toners having a known concentration $C_0$, said printing device having a flow cell where each color toner passes through, said flow cell having at least one windowing area for measuring transmissivity of each of said toners passing through said window, said printing device having memory for storing results of the calibration, said results being stored in a C1 look-up table and a C2 look-up table, including the steps of:

requesting calibration;

measuring a clear voltage value Vc for each of said windowing areas while passing a clear dispersant through said windowing area;

measuring a voltage value V for each of said color toners while passing each of said toners through said windowing area;

determining a low voltage limit for said clear voltage for each of said windowing areas;

placing said low voltage limit in said C2 look-up table as a low voltage endpoint;

determining a high voltage limit for said clear voltage for each of said windowing areas;

placing said high voltage limit in said C2 look-up table as a high voltage endpoint;

calculating $\epsilon x$ for each of said color toners using said clear voltage value Vc, where $\epsilon$ is an optical absorption coefficient of toner, and x is a thickness of said windowing areas, said voltage value V and said known concentration $C_0$;

calculating a clear voltage step size for said C2 look-up table;

calculating remaining clear voltage values for said C2 look-up table;

calculating a C2 concentration value for each of said clear voltage values in said C2 look-up table;

determining a voltage range for each of said color toners, said voltage range being determined by an allowable range of concentrations for each of said toners, as well as said high and said low clear voltage limits;

determining a low C1 concentration limit for each of said color toners;

determining a high C1 concentration limit for each of said color toners;

placing said high C1 concentration limit in said C1 look-up table as a high C1 concentration endpoint for each of said color toners;

calculating a C1 concentration step size for said C1 look-up table for each of said color toners;

calculating remaining C1 concentration values for said C1 look-up table for each of said color toners;

calculating a concentration voltage V corresponding to said C1 concentration values for each of said toners in said C1 look-up table; and placing said C2 table and said memory to be used by said printing device to measure toner concentration.

6. A method for measuring concentration of toner particles carried in a fluid medium in an electrographic printing device, said printing device having a plurality of color toners, said printing device having a flow cell where each color toner passes through, said flow cell having at least one windowing area for measuring a voltage of each of said toners passing through said window, said printing device having memory for storing results of a calibration, including the steps of:

a) generating a C1 look-up table and a C2 look-up table during a calibration cycle of said printing device, said C1 table having color voltage values and corresponding color concentration values for each of said color toners, said C2 table having clear dispersant voltage values and corresponding clear dispersant concentration values, said C1 table and said C2 table being stored in said memory;

b) measuring transmissivity of clear dispersant through said flow cell resulting in a clear voltage value;

c) reading a clear dispersant concentration value from said C2 table corresponding with said clear voltage value;

d) measuring the transmissivity said color toner through said flow cell resulting in a toner voltage value;

e) reading a color toner concentration value from said C1 table corresponding with said toner voltage value;

f) adding said clear dispersant concentration value to said color toner concentration value resulting in a total concentration value; g) using said total concentration value to adjust the concentration of material in said fluid medium corresponding to said color toner; and repeating steps b through g for each of said color toners in said printing device.

7. A system for measuring concentration of a material carried in a fluid medium, comprising:

a flow cell through which said fluid medium passes for measuring properties of a fluid medium passing through said flow cell;

a first delivery system for delivering a first fluid containing material carried in fluid medium;

a second delivery system for delivering a clear dispersant fluid; a switch for selecting among said delivery systems, said switch connecting one of said delivery systems to said flow cell;

a generator for creating a table of C1 concentration and associated voltage values corresponding to the property measured of said first fluid through said flow cell, said table of C1 concentration and associated voltage values being derived during self calibration of said system;

a generator for creating a table of C2 concentration and associated voltage values corresponding to the property measured of said clear dispersant through said flow cell, said table of C2 concentration and associated voltage values being derived during self calibration of said system;

a first memory for storing said table of C1 concentration and associated voltage values;

a second memory for storing said table of C2 concentration and associated voltage values; and an adder for summing a C1 concentration value from said C1 table with a C2 concentration value from said C2 table thereby determining said concentration of said material in said fluid medium being measured by said system.

* * * * *